United States Patent [19]

Ploger et al.

[11] 3,941,772

[45] Mar. 2, 1976

[54] AZACYCLOALKANE-2,2-DIPHOSPHONIC ACIDS

[75] Inventors: Walter Ploger, Hilden, Rhineland; Manfred Schmidt-Dunker, Dusseldorf; Christian Gloxhuber, Haan, Rhineland, all of Germany

[73] Assignee: Henkel & Cie G.m.b.H., Dusseldorf-Holthausen, Germany

[22] Filed: Aug. 20, 1974

[21] Appl. No.: 499,000

[30] Foreign Application Priority Data

Aug. 27, 1973 Germany............................ 2343196

[52] U.S. Cl.............. 260/239 B; 252/136; 252/180; 424/199; 424/200; 424/54; 260/270 K; 260/239 EP; 260/293.51; 260/326.61; 106/111; 106/313; 106/315

[51] Int. Cl.²............................................ C07F 9/38

[58] Field of Search ....... 260/239 B, 270 K, 293.51, 260/326.61, 239 EP

[56] References Cited
UNITED STATES PATENTS 3,846,420   11/1974   Wollman........................ 260/293.51

*Primary Examiner*—Alton D. Rollins
*Assistant Examiner*—Mark L. Berch
*Attorney, Agent, or Firm*—Hammond & Littell

[57] ABSTRACT

Azacycloalkane-2,2-diphosphonic acids having the formula

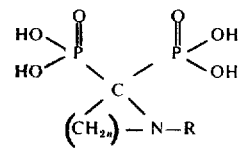

wherein R is a member selected from the group consisting of hydrogen and alkyl having from 1 to 3 carbon atoms and $n$ is an integer from 3 to 5; as well as their water-soluble salts. The azacycloalkane-2,2-diphosphonic acids are excellent sequestering agents especially for alkaline earth metal ions. They are stabilizers for percompounds and are useful in the delaying of the setting times for gypsum.

In addition, the compound are useful in cosmetic preparations such as toothpastes and mouthwashes where they prevent formation of tartar and plaque and are useful in therapy in the treatment of diseases related to the abnormal deposition or dissolution of difficulty soluble calcium salts in the animal body.

8 Claims, No Drawings

AZACYCLOALKANE-2,2-DIPHOSPHONIC ACIDS

OBJECTS OF THE INVENTION

An object of the present invention is the development of an azacycloalkane-2,2-diphosphonic acid derivative selected from the group consisting of (A) a compound of the formula

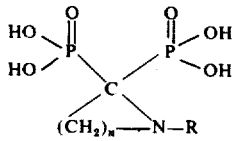

wherein R is selected from the group consisting of hydrogen and alkyl having 1 to 3 carbon atoms, and n is an integer from 3 to 5; and (B) a water-soluble salt thereof.

Another object of the present invention is the development of a process for the production of the above azacycloalkane-2,2-diphosphonic acids or their water-soluble salts.

Another object of the present invention is the development of a process for the delaying or inhibiting of the precipitation of alkaline earth metal ions from solution by the use of stoichiometric to sub-stoichiometric amounts of the above azacycloalkane-2,2-diphosphonic acids or their water-soluble salts.

A further object of the present invention is the development of a method for delaying the setting time for gypsum which comprises adding to the mixture of plaster materials and water a small amount of the above azacycloalkane-2,2-diphosphonic acids or their water-soluble salts.

A yet further object of the present invention is the development of a method for the treatment of diseases in warm-blooded animals related to the abnormal deposition or dissolution of difficulty soluble calcium salts which comprises administering a safe but effective amount of at least one of the above azacycloalkane-2,2-diphosphonic acids or their water-soluble salts to the warm-blooded animal.

These and other objects of the invention will become more apparent as the description thereof proceeds.

DESCRIPTION OF THE INVENTION

The above objects have been achieved by the development of new azacycloalkane-2,2-diphosphonic acid derivatives selected from the group consisting of a compound of the formula I

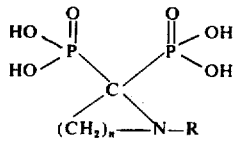    I wherein R is selected from the group consisting of hydrogen and alkyl having 1 to 3 carbon atoms, preferably methyl, and n is an integer from 3 to 5; and (B) a water soluble salt thereof.

It has now been found that the above novel phosphorus compounds having the formula I or their water-soluble salts are obtained when a lactam having the formula

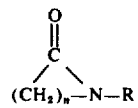    II in which n is an integer of from 3 to 5 and R is hydrogen or alkyl having 1 to 3 carbon atoms, preferably methyl, is reacted with phosphorus trihalide or phosphorous acid and phosphorous trihalides; and then the reaction product is hydrolyzed and, if necessary, is converted into the salts.

More particularly, according to the present invention the process for the preparation of the azacycloalkane-2,2-diphosphonic acid derivative of formula I comprises the steps of reacting a lactam having the formula

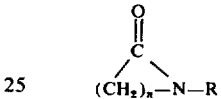

wherein R and n have the same meanings as defined above with at least the stoichiometric amount of a phosphorus reactant selected from the group consisting of a phosphorus trihalide and a mixture of a phosphorus trihalide and phosphorous acid subjecting the resulting reaction product to a hydrolysis by the action of an aqueous media selected from the group consisting of water and an aqueous alkali metal hydroxide solution, and recovering said azacycloalkane-2,2-diphosphonic acid derivative.

In general, the reaction is carried out at temperatures between 40°C and 150°C. Suitable starting materials are lactams having 3 to 5 carbon atoms, for example, pyrrolidone, N-methylpyrrolidone, piperidone, and caprolactam, which are readily accessible and available as technical products. The above reaction can be so carried out, for example, that the above-named lactam is first melted with phosphorous acid, and that $PCl_3$ is slowly added while stirring.

Subsequently, the reaction product thus formed is hydrolyzed. The molten lactam can be also be reacted directly with phosphorus trihalides and can then be hydrolyzed stepwise. Suitable phosphorus trihalides are preferably phosphorus trichloride and phosphorus tribromide. The latter has proven to be especially preferred when lactams are charged without the addition of phosphorous acid. The molar ratio of the lactam to the phosphorus compound ranges between 1 : 2 to 1 : 6 preferably about 1 : 4.

It is advantageous to hydrolyze the reaction product by the addition of water to the reaction mixture. If so desired, one can also carry out the hydrolysis in the presence of an alkali metal hydroxide, especially in the presence of sodium hydroxide or potassium hydroxide. In many cases, the novel diphosphonic acids can be also utilized in form of their water-soluble salts, such as the alkali metal salts, especially the lithium salt, sodium salt, or potassium salt, or also the ammonium salt. Insofar as the azacycloalkane-2,2-diphosphonic acids are obtained in the form of the acids, these acids can readily be converted into the water-soluble salts, for example, by partial or total neutralization with the corresponding bases.

The salts correspond to the following formula:

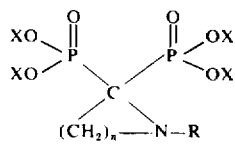

III wherein X is hydrogen, $NH_4$ or a metal cation, with the proviso that, at the most, 3 hydrogen atoms are present.

Specific examples of the novel azacycloalkane-2,2-diphosphonic acids according to the present invention include
azacyclopentane-2,2-diphosphonic acid,
N-methyl-azacyclopentane-2,3-diphosphonic acid,
azacyclohexane-2,2-diphosphonic acid, and
azacycloheptane-2,2-diphosphonic acid.

The novel 2,2-diphosphono-azacycloalkanes embraced by Formula I above are excellent sequestering agents for polyvalent metal ions, particularly di- and tri-valent metal ions. They are particularly suitable as sequestering agents for alkaline earth metal ions, so that they can be used for many technical applications, such as in detergents and cleansers, as well as in water treatment. They can be employed in stoichiometric and substoichiometric amounts as sequestering agents for alkaline earth metal ions. They also have a stabilizing effect on percompounds.

They are also suitable as additives to delay the setting time of gypsum and as ceramic slip liquifiers. For delaying the setting time of gypsum, the sodium, potassium or ammonium salts, in addition to the acids, can also be used. The corresponding lithium salts as well as zinc and magnesium salts are likewise suitable.

Furthermore, the novel compounds can be used in preparations such as mouth washes and tooth pastes in order to avoid the formation of tartar or plaque. For the prevention of tartar, these preparations can contain the free diphosphonic acids, as well as their non-toxic pharmacologically acceptable salts, such as the sodium salt, potassium salt, ammonium salt, and substituted ammonium salts, such as the mono-, di-, or triethanolammonium salts. The partial salts in which only a portion of the hydrogens is replaced by other cations can be used as well as the completely substituted salts which can be used.

Preferable are these salts which are approximately neutral in an aqueous solution (pH 5 to 9). Mixtures of the above-named salts can also be used.

The stability of the compounds embraced by Formula I to be used according to the invention for tartar treatment and prophylaxis, results from their capacity of inhibiting the formation of crystals in the precipitation of calcium apatite already in small amounts. Calcium apatite, which is precipitated in the presence of the diphosphonic acids, according to the invention, is X-ray amorphous, in contrast to crystalline apatite, which is usually formed without this addition.

The novel 2,2-diphosphono-azacycloalkane compounds according to the invention and their water-soluble alkali metal and ammonium salts are suitable as pharmacologically active substances in pharmaceutical dosage unit compositions. They have therapeutic and/or prophylatic effects in the treatment of a number of diseases, which are related to the abnormal deposition or dissolution of difficultly soluble calcium salts in the animal body. These diseases can be divided into two catgeories:

1. Abnormal depositions of difficultly soluble calcium salts, mostly calcium phosphate, cause bone malformations, pathological hardening of tissues and secretions in organs.
2. The abnormal dissolution of hard tissues causes losses of hard bone substance, which cannot be replaced or are replaced only by incompletely crystallized tissue. This dissolution is frequently accompanied by pathologically high calcium and phosphate concentrations in the plasma.

These diseases include: osteoporosis, osteodystrophy, Paget's disease, myositis ossificans, Bechterew's disease, cholelithiasis, nephrolithiasis, urinary calculus, hardening of the arteries (sclerosis), arthritis, bursitis, neuritis, tetany.

In addition to the free azacycloalkane-2,2-diphosphonic acids, their pharmacologically harmless salts, such as the alkali metal salts, for example, the sodium or potassium salts, or the ammonium salts or the substituted ammonium salts, such as the lower alkanol ammonium salts for example the mono-, di-, or triethanol ammonium salts can be used, for use in pharmaceutical preparations in the treatment of these diseases or for their prophylaxis. Both the partial salts, in which only a portion of the acid protons are replaced by other cations, and complete salts can be used, but partial salts, which react substantially neutral in aqueous solution (pH 5 to 9) are preferred. Mixtures of the above-mentioned salts can likewise be used.

The dosage range of the 2,2-diphosphono-azacycloalkanes can be from 0.05 to 500 mg per kg of the warm-blooded animal body weight. The preferred dose is 1 to 20 mg per kg of body weight, and can be administered up to four times daily. The higher doses are necessary for oral application, due to the limited resorption. Doses under 0.05 mg per kg of body weight have little effect on the pathological calcification or dissolution of bone substance. Doses above 500 mg/kg of body weight may have toxic side effects in the long run. The compounds embraced by Formula I above can be administered orally, subcutaneously or intraperitoneally in the form of tablets, pills, capsules or as injectable solutions. For certain warm-blooded animals these compounds can also be used as part of the feed or feed additives.

The following examples are merely illustrative of the present invention without being deemed limitative in any manner thereof.

EXAMPLE 1

Azacyclopentane-2,2-diphosphonic acid

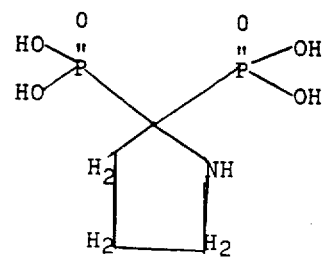

85.0 gm of 2-pyrrolidone (1.0 mol) and 164 gm of H₃PO₃ (2.0 mols) were melted at 80°C. While stirring this melt, 176 ml of PCl₃ (2.0 mols) were added thereto. The mixture was stirred for three additional hours and was left standing at 70°C overnight. Then, three liters of H₂O were used for the hydrolysis. The solution was boiled with activated carbon; and after filtration, the reaction product was precipitated with acetone. The white substance was dissolved in water, and passed over a cation exchanger. The solution was concentrated; and the substance was separated upon the addition of ethanol. The yield of crystalline azacyclopentane-2,2-diphosphonic acid was 95 gm, or about 41% of the theory. The molecular weight of the compound was determined by titration to be 230 (calculated: 231.09).

Elemental Analysis: Calculated: 20.79%C; 4.80%H; 6.06%N; 26.81%P; Found: 20.64%C; 4.48%H; 6.04%N; 25.79%P In the IR-spectrum, the compound showed a $\delta_{NH}$-band at 1615 cm⁻¹. The compound has a melting point of 277°C.

EXAMPLE 2

N-methyl-azacyclopentane-2,2-diphosphonic acid

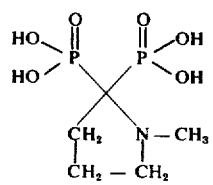

99 gm of N-methyl-2-pyrrolidone (1.0 mol) and 164 gm of H₃PO₃ (2.0 mols) were melted at 80°C and reacted with PCl₃ utilizing a procedure analogous to that described in Example 1. The reaction mixture was worked up analogously to that described in Example 1. The product which was oily, at first, crystallized after the addition of ethanol and after standing for a while. The yield of crystalline N-methyl-azacyclopentane-2,2-diphosphonic acid was 54 gm, or about 21% of theory. After drying at 60°C in a drying oven, the substance was separated as a monohydrate having a titrimetrically determined molecular weight of 261 (calculated:263.133).

Elemental Analysis: Calculated: 22.82%C; 5.75%H; 5.32%N; 23.54%P; Found: 23.11%C; 5.67%H; 5.01%N; 23.37%P The anhydrous compound was obtained after drying at 80°C over P₂O₅.

Elemental Analysis: Calculated: 24.50%C; 5.35%H; 5.71%N; Found: 24.28%C; 5.43%H; 5.23%N In the IR-spectrum of the anhydrous compound, no absorption was observed in the range from 1500–1800 cm⁻¹. The compound had a m.p. of 207°C.

EXAMPLE 3

Azacyclohexane-2,2-diphosphonic acid

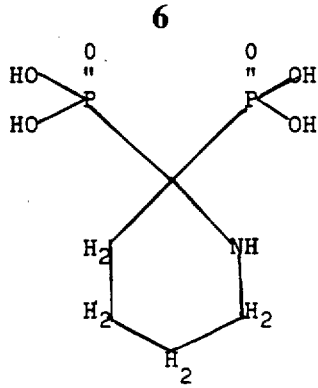

49.5 of 2-piperidone (0.5 mol) and 82 gm of H₃PO₃ (1.0 mol) were melted at 70°C and reacted with 88 ml of PCl₃ using a procedure analogous to that described in Example 1. The reaction mixture was worked up analogously to that described in Example 1. The yield of crystalline diphosphonic acid was 28 gm, or about 21% of the theory. After drying at 60°C in a drying oven, the compound was obtained as the monohydrate. The titrimetrically determined molecular weight was 261 (calculated: 263.1).

Elemental Analysis: Calculated: 22.82%C; 5.75%H; 5.32%N; 23.54%P; Found: 23.59%C; 5.29%H; 5.61%N; 24.15%P The anhydrous compound, azacyclohexane-2,2-diphosphonic acid, was obtained after drying at 80°C over P₂O₅. The IR-spectrum showed the $\delta_{NH}$-band at 1585 cm⁻¹. The compound has a melting point of 249°C.

EXAMPLE 4

Azacycloheptane-2,2-diphosphonic acid

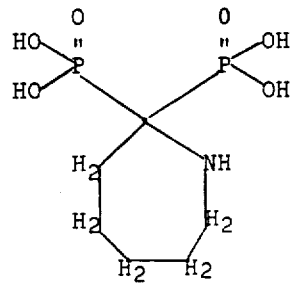

a. 113 gm of caprolactam (1.0 mol) and 164 gm of H₃PO₃ (2.0 mols) were heated at 100°C until a clear melt was obtained. After cooling to 70°C, reaction with 176 ml of PCl₃ (2.0 mols) was carried out using a procedure analogous to that described in Example 1. The reaction mixture was worked up analogous to the procedure described in Example 1. The yield of crystalline azacycloheptane-2,2-diphosphonic acid which was difficulty water-soluble was 84 gm, or about 32% of the theory.

b. 65.5 gm of caprolactam (0.5 mol) were melted at 80°C, and 190 ml of PBr₃ (2.0 mols) were slowly added thereto. After four hours, hydrolysis were carried out by the slow addition of 100 ml of water; and an additional 400 ml of water were added to the reaction mixture. The working-up was carried out using a procedure analogous to that described in Example 1. The yield of crystalline azacycloheptane-2,2-diphosphonic acid was 33 gm, or about 25% of theory.

c. 56.5 gm of caprolactam (0.5 mol) were dissolved in 300 ml of dioxane at 70°C, and 190 ml of $PBr_3$ (2.0 mols) were slowly added dropwise. After four hours, hydrolysis was effected by the slow dropwise addition of 500 ml of water. After boiling with activated carbon and filtration, the dioxane phase was separated, and the aqueous phase was worked up analgously to the procedure described in Example 1. The yield of azocycloheptane-2,2-diphosphonic acid was 24 gm, or about 18% of theory. After drying at 80°C in a vacuum drying oven, the substance has a titrimetrically determined molecular weight of 260 (calculated: 259.1).

Elemental Analysis: Calculated: 27.81%C; 5.83%H; 5.41%N; 23.91%P; Found 27.71%C; 5.64%H; 5.37%N; 23.60%P In the IR-spectrum of the compound, the $\delta_{NH}$-band was at 1610 cm$^{-1}$. The compound has a m.p. of 257°C.

EXAMPLE 5

Sequestering of calcium

In the investigation of the sequestering of calcium, a modified Hampshire Test was employed and worked as follows 1 gm of the sequestering agent was dissolved in 50 ml of $H_2O$, adjusted with NaOH to a pH of 11. 50 ml of a $Ca^{++}$ solution (1470 mgm of $CaCl_2.2H_2O$/l) were mixed with 100 ml of a sodium carbonate solution (7.15 gm $Na_2CO_3$. 10 $H_2O$/l.). Then the solution of the sequestering agent was added dropwise from a burette until the calcium carbonate precipitate was redissolved. The values found have been reported in Table I. For the sake of simplicity, only the value of n and the various substituents for R according to formula I are indicated in the left column of the Table.

TABLE I

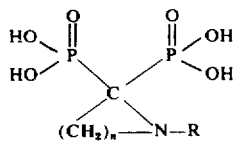

I wherein R is selected from the group consisting of hydrogen and alkyl having 1 to 3 carbon atoms, and n is an integer from 3 to 5.

| Compound | | Consumption of Sequestering Agent Solution (ml) | mgm of CaCO₃ Sequestered per gm of Compound |
|---|---|---|---|
| n | R | | |
| 3 | H | 3.6 | 695 |
| 3 | CH₃ | 2.6 | 960 |
| 4 | H | 3.3 | 760 |
| 5 | H | 3.4 | 735 |

Practically identical results were obtained if, instead of the acids, the corresponding sodium, potassium or ammonium salts were employed.

EXAMPLE 6

Threshold Effect

The Hampshire Test at room temperature and the Sodium Carbonate Silicate Test at 60°C, as well as at 95°C, were used for studying the prevention of the precipitation of difficultly-soluble calcium compounds when substoichiometric amounts of sequestering agents were utilized, as follows:

a. Hampshire Test:
200 mgm of the sequestering agent were dissolved in 10 ml of $H_2O$ (which has been adjusted with NaOH to pH 11); and 100 ml of sodium carbonate solution (14.3 gm of $Na_2CO_3$ . $H_2O$/liter) were added. A calcium solution (36.8 gm of $CaCl_2$. $2H_2O$/liter) was added dropwise from a burette until the cloudiness formed barely remains.

For an explanation of the data in the two left columns of the following Table II, see Example 5.

TABLE II

| Compound | | Consumption of Ca-Solution ml | mgm CaCO₃ | mgm of CaCO₃ Sequestered per gm of Compound |
|---|---|---|---|---|
| n | R | | | |
| 3 | H | 7.8 | 195 | 975 |
| 3 | CH₃ | 13.5 | 338 | 1690 |
| 4 | H | 8.5 | 212 | 1060 |
| 5 | H | 8.5 | 212 | 1060 | b. Sodium Carbonate - Silicate Test
25 ml of water having a German hardness of 80° (Ca : Mg = 4 : 1) in a 100 ml graduated cylinder were treated with the sequestering agent solution (7.5 mgm or 15.0 mgm). After dilution with distilled water up to a volume of 65 to 70 ml, 25 ml of a sodium carbonate - sodium silicate solution having a concentration of 4.5 gm of $Na_2CO_3$/liter and 600 mgm of sodium silicate/liter (in a ratio of $SiO_2$ : $Na_2O = 3.36 : 1$) were added. After filling up to the 100 ml mark, the sample was either heated to 60°C within 20 minutes and maintained at this temperature for an additional 10 minutes (see Table III for the results of this procedure); or the sample was heated to 95°C within 25 to 30 minutes and maintained at 95°C for an additional 30 minutes. (See Table IV for the results of this procedure).

Subsequently, the solution, the precipitated portion, and the incrustation tightly adhering to the glass were analyzed as to their calcium content. In Table III and Table IV, the results of the analyses are expressed in percent whereby the sum of the resulting values is set equal to 100%. For an explanation of the data specified in the two left columns, see Example 5.

TABLE III

| Compound | | | 150 mgm/liter of sequestering agent, 60°C | |
|---|---|---|---|---|
| n | R | CaO Solution | CaO Precipitation | CaO Incrustation |
| 3 | H | 99.1 | 0.8 | 0.1 |
| 3 | CH₃ | 99.0 | 0.9 | 0.1 |
| 4 | H | 98.8 | 1.1 | 0.1 |
| 5 | H | 79.8 | 20.1 | 0.1 |

TABLE IV

| Compound n | R | 150 mg/liter of sequestering agent, 95°C | | | 75 mg/liter of sequestering agent, 95°C | | |
|---|---|---|---|---|---|---|---|
| | | CaO Soln. | CaO Pptd. | CaO Incrust. | CaO Soln. | CaO Pptd. | CaO Incrust. |
| 3 | H | 99.0 | 0.9 | 0.1 | 88.8 | 11.1 | 0.1 |
| 3 | $CH_3$ | 92.2 | 7.7 | 0.1 | 71.1 | 28.6 | 1.3 |
| 4 | H | 99.0 | 0.9 | 0.1 | 98.4 | 1.5 | 0.1 |
| 5 | H | 80.0 | 19.9 | 0.1 | — | — | — |

Practically identical results were obtained in Tables III and IV, if, instead of the acids, the corresponding sodium, potassium or ammonium salts were employed.

EXAMPLE 7

Delay in the setting of gypsum

Gypsum materials in the form of plaster, plaster of Paris, or in mixture with aggregates, like limestone, sand, perlite or cellulose, set relatively fast, so that rapid processing must take place. A delay of the setting time can be achieved with the addition of the above-described azacycloalkanediphosphonic acids, and the processing of the gypsum materials can thus be considerably facilitated.

In the following tests, each of the various azacycloalkane-2,2-diphosphonic acids of the invention was added to the water before the gypsum was mixed. However, water-soluble salts of the phosphonic acids, particularly the lithium, sodium, potassium and ammonium salts can also be mixed instead with the gypsum or added shortly after the mixing of the gypsum material together with the water. Specifically the following setting values were found and reported in Table V, using in each test 20.0 gm of gypsum and 9 ml of $H_2O$. The setting time is the time interval in which the gypsum was spreadable and easy to handle.

For the explanation of the data in the left column of Table V, see Example 5.

TABLE V

| Compound n | R | Amount (mgm) | Setting Time (min.) |
|---|---|---|---|
| — | — | — | 15 |
| 3 | H | 25 | 60 |
| 3 | $CH_3$ | 25 | 50 |
| 4 | H | 25 | 50 |
| 5 | H | 25 | 40 |

Comparable results were obtained by using the corresponding magnesium and zinc salts.

EXAMPLE 8

Pharmaceutical application a. Apatite crystallization delay test in vitro

The compounds prepared according to the invention are efficient in preventing abnormal calcium depositions. Their efficacy in this respect was demonstrated in vitro by their retarding the crystallization of apatite.

Supersaturated solutions of $Ca^{++}$ and $HPO_4^{--}$ ions are relatively stable, but crystallize after the addition of an apatite nuclei according to the reaction.

$$5\ Ca^{++} + 3\ HPO_4^{--} + H_2O \rightarrow Ca_5(PO_4)_3OH + 4\ H^+$$

with the release of protons. The reaction can, therefore, be readily observed by titration with a base at a constant pH.

400 ml of 0.0008 molar $KH_2PO_4$ solution were mixed with 45 ml of a 0.012 molar $CaCl_2$ solution, and the clear solution was standardized with KOH to a pH of 7.4, after being brought to a temperature of 35°C. After 30 minutes drying which time the pH did not change, a suspension of 100 mgm of hydroxyl apatite in 50 ml of $H_2O$ was added. The crystallization set in immediately and was followed by "pH-Stat" titration with 0.05 N KOH.

If a small amount of one of the azacycloalkane-2,2-diphosphonic acids of the invention was added to the solution before the apatite was added, the crystallization was greatly delayed.

Table VI gives the values of the delay in crystallization. With respect to the data specified in the two left columns of the Table, see Example 5.

TABLE VI

| Compound n | R | Amount mgm/liter | Decreased of the Crystallization in % after | | |
|---|---|---|---|---|---|
| | | | 4 hrs. | 8 hrs. | 12 hrs. |
| 3 | H | 4 | 84 | 81 | 79 |
| 3 | $CH_3$ | 4 | — | 78 | — |
| 4 | H | 4 | 80 | 73 | 69 |
| 5 | H | 4 | 80 | 80 | 76 | b. Prevention of hardening of the aorta in rats

The effectiveness of the azacycloalkane-2,2-diphosphonic acids of the present invention in preventing abnormal calcium deposits in vivo in rats can be demonstrated as follows.

This test was based on the observation that high doses of vitamin $D_3$ fed to rats cause a considerable hardening of the aorta in rats. 30 Female rats weighing 150 to 200 gm each were divided into three groups of ten animals each. They received during the test period a normal diet and tap water ad libitum. One group of ten animals (control) received no further treatment. Another group of the animals received from 3rd to the 7th day, 75,000 units of vitamin $D_3$ daily through a stomach sound. The third group likewise received from 3rd to the 7th day, 75,000 units of vitamin $D_3$ daily through a stomach sound and, in addition likewise orally, 10 mgm kg of one of the azacycloalkane-2,2-diphosphonic acids from the 1st to the 10th day. After ten days the animals were sacrificed and their aortas prepared and dried for 12 hours at 105°C. After determination of the dry weight the aortas were ashed; the residue was dissolved, and the calcium was determined by flame photometry. The treatment with acacycloalkane-2,2-diphosphonic acid reduced the vitamin $D_3$ induced hardening of the aortas of rats considerably.

EXAMPLE 9

Pharmaceutical preparations

For the production of pharmaceutical preparations in the form of a tablet, the known methods of preparation were followed to produce a tablet having an effective dosage unit composition as follows:

| | |
|---|---|
| 2,2-Diphosphono-azacycloalkane | 100 mgm |
| Lactose | 100 mgm |
| Starch | 47 mgm |
| Magnesium Stearate | 3 mgm |

For the production of pharmaceutical preparations in the form of a capsule, the known methods of preparation are followed to produce a capsule having an effective dosage unit composition as follows:

| 2,2-Diphosphono-azacycloalkane | 100 mgm |
|---|---|
| Starch | 20 mgm |
| Sodium Lauryl Sulfate | 1 mgm |

In the specified compositions for tablets and capsules, the amount of the 2,2-diphosphono-azacycloalkane stated above is the amount used of a compound according to the invention; that is a compound embraced by formula I above, and preferably refers to the amount of 2,2-diphosphono-azacyclopentane, N-methyl-2,2-diphosphono-azacyclopentane,2,2-diphosphonoazacyclohexane, or 2,2-diphosphono-azacycloheptane utilized in the respective composition. In another series of compositions, the free acids in the above formula were replaced by the corresponding amount of the disodium salts of the acids.

EXAMPLE 10

Cosmetic preparations

The following recipes are suitable as a basic formula for tooth pastes:

| | | Parts by Weight |
|---|---|---|
| (a) | Glycerin | 60.0 |
| | Water | 13.5 |
| | Sodium carboxymethyl-cellulose | 0.6 |
| | Silicic acid xerogel | 20.0 |
| | Sodium laurylsulfate | 2.0 |
| | Essential oils | 1.0 |
| | Sweetening agent | 0.4 |
| | 2,2-Diphosphono-azacycloalkane | 2.5 |
| (b) | Glycerin | 30.0 |
| | Water | 18.5 |
| | Sodium carboxymethyl-cellulose | 1.0 |
| | Aluminum hydroxide | 44.0 |
| | Sodium laurylsulfate | 1.0 |
| | Pyrogenic silicic acid | 1.5 |
| | Essential oils | 1.5 |
| | Sweetening agent | 0.5 |
| | 2,2-Diphosphono-azacycloalkane | 2.0 |

Suitable as a basic formulation for mouthwashes is the following recipe:

| | Parts by Weight |
|---|---|
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| 2,2-Diphosphono-azacycloalkane | 2.5 |

The stated amount of 2,2-diphosphono-azacycloalkane used refers to the amount used of a compound according to the invention; that is a compound embraced by formula I above, and preferably refers to the amount of 2,2-diphosphono-azacyclopentane, N-methyl-2,2-diphosphono-azacyclopentane, 2,2-diphosphonoazacyclohexane, or 2,2-diphosphono-azacycloheptane utilized.

By regular use of the mouthwashes and/or toothpastes containing the above-mentioned azacycloalkane-diphosphonic acids, according to the invention, the formation of tartar could be considerably reduced. The formation of hard compact plaque on the teeth was to a great extent prevented.

The preceding specific embodiments are illustrative of the practice of the invention. It is to be understood, however, that other expedients known to those skilled in the art or discussed herein may be employed without departing from the spirit of the invention or the scope of the appended claims.

We claim:

1. An azacycloalkane-2,2-diphosphonic compound selected from the group consisting of (A) a compound of the formula

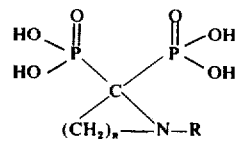

wherein R is selected from the group consisting of hydrogen and alkyl having 1 to 3 carbon atoms, and $n$ is an integer from 3 to 5; and (B) a non-toxic, pharmacologically-acceptable water-soluble salt thereof.

2. The azacycloalkane-2,2-diphosphonic compound of claim 1, wherein R is selected from the group consisting of hydrogen and methyl and $n$ is an integer from 3 to 5.

3. The azacycloalkane-2,2-diphosphonic compound of claim 1, wherein R is hydrogen and $n$ is 3.

4. The azacycloalkane-2,2-diphosphonic compound of claim 1, wherein R is methyl and $n$ is 3.

5. The azacycloalkane-2,2-diphosphonic compound of claim 1, wherein R is hydrogen and $n$ is 4.

6. The azacycloalkane-2,2-diphosphonic compound of claim 1, wherein R is hydrogen and $n$ is 5.

7. The azacycloalkane-2,2-diphosphonic compound of claim 1, wherein said non-toxic, pharmacologicallyacceptable water-soluble salt is a member selected from the group consisting of alkali metals, ammonium, lower alkanolammonium, zinc and magnesium.

8. The azacycloalkane-2,2-diphosphonic compound of claim 7, wherein said water-soluble salts are substantially neutral with a pH of 5 to 9 in an aqueous solution.

* * * * *